United States Patent [19]

Adam

[11] Patent Number: 5,092,461
[45] Date of Patent: Mar. 3, 1992

[54] NEEDLE COVER ASSEMBLY

[76] Inventor: John M. Adam, 818 Colestone Rd., Marietta, Cobb, Ga. 30060

[21] Appl. No.: 268,503

[22] Filed: Nov. 8, 1988

[51] Int. Cl.$^5$ .................................................. A61M 5/00
[52] U.S. Cl. ..................................... 206/365; 604/263; 604/192; 604/198
[58] Field of Search ................ 206/365; 604/187, 192, 604/193, 263, 198

[56] References Cited

U.S. PATENT DOCUMENTS

| | | | |
|---|---|---|---|
| 2,110,123 | 3/1938 | Eisele | 206/365 |
| 4,643,722 | 2/1987 | Smith, Jr. | 206/365 X |
| 4,664,259 | 5/1987 | Landis | 206/365 |
| 4,725,267 | 2/1988 | Vaillancourt | 604/192 |
| 4,735,618 | 4/1988 | Hagen | 604/192 |
| 4,747,836 | 5/1988 | Luther | 604/263 X |
| 4,795,443 | 1/1989 | Permenter et al. | 604/263 X |

FOREIGN PATENT DOCUMENTS 2202446  9/1988  United Kingdom ................ 604/263

Primary Examiner—William I. Price
Attorney, Agent, or Firm—B. J. Powell

[57] ABSTRACT

A needle cover assembly for a needle with a clamp to slidably clip the assembly onto the needle support, a needle enclosure to fit over the needle tip and an extension connecting the clamp with the needle enclosure so that the needle can be covered in a one-handed operation.

9 Claims, 3 Drawing Sheets

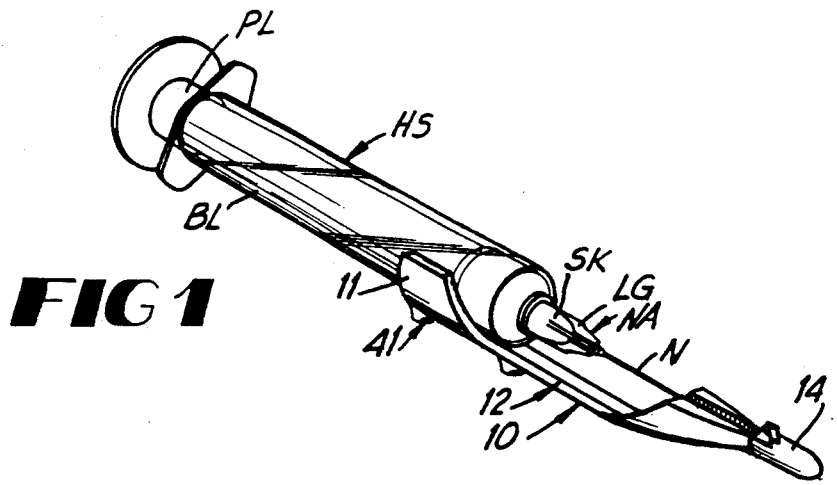
FIG 1
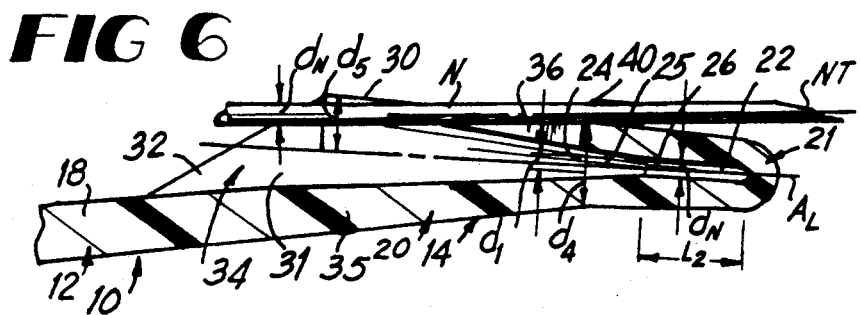
FIG 6
FIG 7
FIG 8

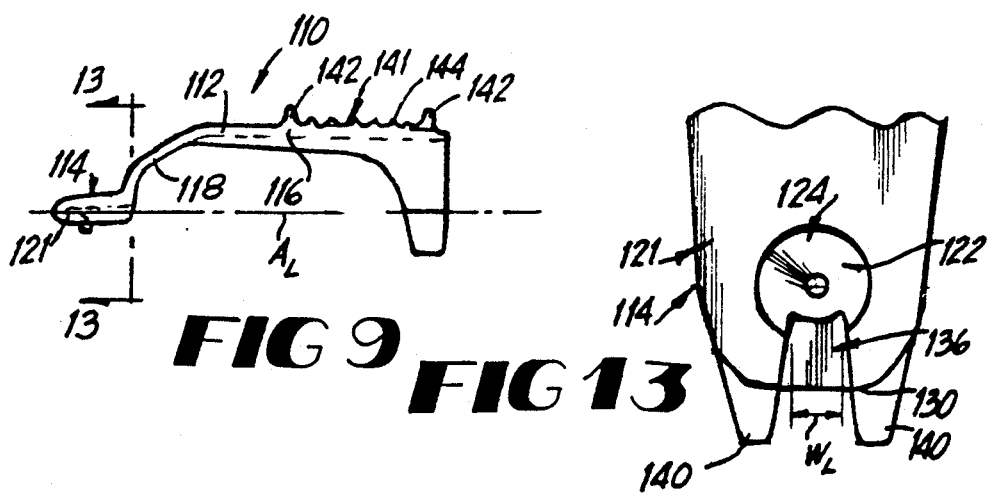
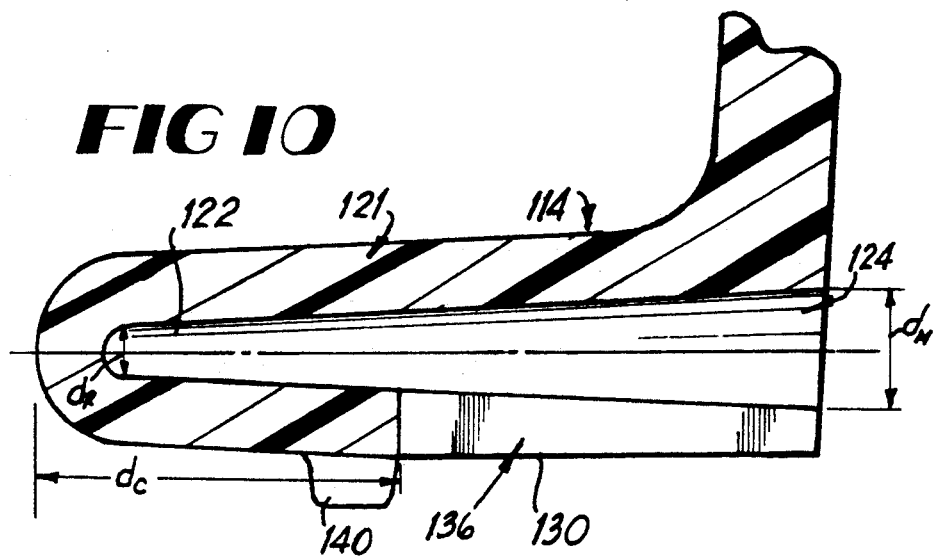
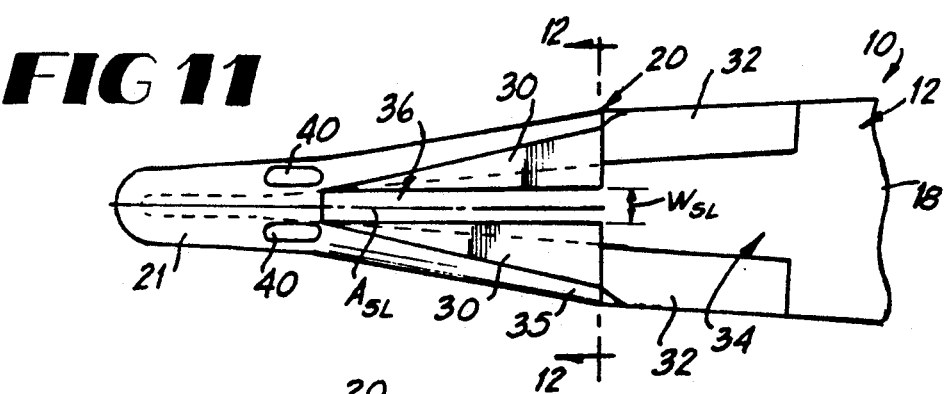
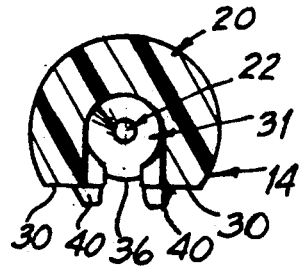

NEEDLE COVER ASSEMBLY

BACKGROUND OF THE INVENTION

This invention relates generally to needle covers and more particularly to needle covers used to enclose contaminated needles without accidental puncture of the attendant using same.

Various kinds of medical devices use needles to inject or withdraw fluids from humans or animals. Typical of such medical devices are hypodermic syringes and blood withdrawal devices using vacuum containers and the like. Typically, the needles for such devices are supplied from the manufacturer in a covered condition so as to maintain the sterility of the needle, which cover is removed prior to use. After use, such covers are typically reapplied to the contaminated needle to isolate it from the medical attendant and from anyone subsequently handling the needle which is thrown away after one use. One of the primary problems with such prior art needle covers is that the medical attendants can accidentally puncture themselves or someone else as the needle is being reinserted into the cover or being carried with the needle exposed. Since these needles are frequently being used on patients which have serious blood borne diseases, the contamination of the needle after use can be transferred to anyone accidentally punctured with the needle thus infecting this person with the blood borne disease. This frequently produces serious side effects with infectious diseases such as hepatitus, AIDS, or the like.

The following patents are indicative of the prior art:

| Patent No. | Inventor | Issue Date | Class |
| --- | --- | --- | --- |
| 2,047,010 | F. S. Dickinson | 07/07/36 | 604/117 |
| 2,198,666 | B. Gruskin | 04/30/40 | 604/117 |
| 2,457,464 | L. L. Grose | 12/28/48 | 604/117 |
| 2,854,976 | S. E. Heyduck | 10/07/58 | 604/117 |
| 3,658,061 | J. P. Hall | 04/25/72 | 128/214.4 |
| 4,659,330 | R. Nelson, et al | 04/21/87 | 604/192 |

U.S. Pat. No. 3,658,061 is directed to a cathether needle guard that snaps over the needle to cover it. Because the side opening in the guard is relatively small, and because the guard has to be forced sidewise over the needle, such a device is relatively difficult to manually manipulate to make sure that the needle passes within the guard. Secondly, the sidewise force required to force the guard over the needle may be difficult to control sufficiently to prevent breaking the needle.

U.S. Pat. No. 4,659,330 shows a syringe needle guard designed to be placed over the needle after use. This guard is relatively complicated in construction thereby requiring expensive manufacturing procedures and also relatively difficult to use since the tip of the needle must pass through a relatively small opening in the guard in order to be used.

U.S. Pat. No. 2,854,976 shows a needle guard for a syringe which partially encloses the needle tip. This guard requires two hands to use and is difficult to operate.

U.S. Pat. No. 2,047,010; 2,198,666 and 2,457,464 disclose various guides used with needles or surgical instruments to assist in using the implement. Such guides do not cover or fully protect the tip of the needle or surgical instrument.

SUMMARY OF THE INVENTION

These and other problems and disadvantages associated with the prior art are overcome by the invention disclosed herein by providing a needle cover which is supported on the hyprodermic syringe or vacuum container as the needle is used and which can be subsequently placed over the needle after use with one hand. The needle cover provides maximum protection for the attendant during and after placement of the cover over the needle and is simple to manufacture and use.

The apparatus of the invention includes a needle cover which is provided with an arcuate clamp at one end to slidable clip over the barrel of the syringe or vacuum container and to be manually slipped therealong. An elongate flexible extension on the clamp projects forwardly therefrom and mounts a needle enclosure on the projecting end thereof opposite the clamp. The extension is sufficiently flexible to allow the enclosure to be pulled up onto the base of the needle on the syringe or vacuum container so that it will be located out of the way during use. The enclosure is provided with a pair of guide flanges which project out from one side of the needle enclosure to guide the needle enclosure relative to the needle as the needle enclosure is pushed from the base of the needle out past the tip of the needle. The needle enclosure is provided with a passage therein that defines an opening thereto facing the tip of the needle when the needle enclosure is moved out past the tip of the needle so that the tip of the needle enters the passage as the attendant pulls the needle enclosure back toward the tip of the needle. The passage in the enclosure is sized to provide a line-to-line fit with the needle tip to prevent drainage from the needle tip with the depth of the passage being sufficient to fully enclose the tip of the needle. A finger grip is provided on the extension adjacent to the arcuate clamp to be engaged by the attendant's thumb of finger to move the cover back and forth along the length of the syringe so that the needle enclosure can pass along the length of the needle, drop over the tip thereof and be retracted back over the tip of the needle to enclose the needle tip.

These and other features and advantages of the invention will become more clearly understood upon consideration of the following detailed description and accompanying drawings wherein like characters of references designate corresponding parts of several views and in which:

BRIEF DESCRIPTION OF THE DRAWINGS

FIG. 1 is a perspective view of the invention in use;

FIG. 6 is an enlarged longitudinal cross-sectional view of the needle enclosure;

FIG. 7 is a view similar to FIG. 6 showing the invention extending past the hypodermic needle;

FIG. 8 is a view similar to FIG. 7 showing the invention inserted over the tip of the needle;

FIG. 9 is a side elevational view of a second embodiment of the invention for vacuum containers;

FIG. 10 is an enlarged longitudinal cross-sectional view of the needle cover in FIG. 9;

FIG. 11 is an enlarged partial bottom view of the invention of FIG. 1;

FIG. 12 is a cross-sectional view taken along line 12—12 in FIG. 11; and

FIG. 13 is a view taken along line 13—13 in FIG. 9.

Figure 2:
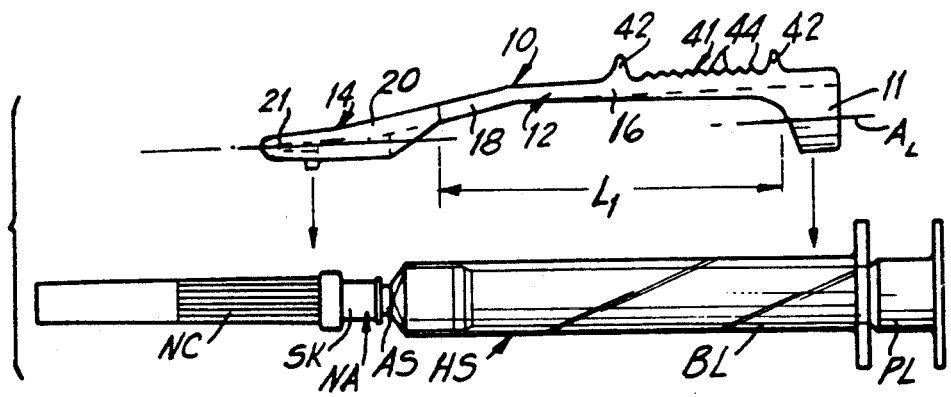
FIG. 2 is a side elevational view of a first embodiment of the invention exploded away from a hypodermic syringe.

These figures and the following detailed description disclose specific embodiments of the invention, however, the inventive concept is not limited thereto since it may embodied in other forms.

DETAILED DESCRIPTION OF ILLUSTRATIVE EMBODIMENTS

The invention covers various types of needles used to inject and/or withdraw fluids from human and animal bodies, especially those needle assemblies which are likely to be contaminated with infectious diseases. While numerous types of needle assemblies may be used by the medical profession, a common type associated with hyprodermic syringes is illustrated. It is also understood that the inventive concept may be applied to any type needle assembly.

The needle assembly illustrated is seen in FIGS. 1–8 and is designed to slip on the end of a hypodermic syringe HS or other type holder. The needle assembly NA illustrated includes a socket member SK which fits over the needle attachment section AS on the hypodermic syringe HS. The socket member SK has an internal tapered passage therein for force fit on the section AS or may be threaded. The needle assembly NA also includes a needle N which is mounted in the socket member SK and projects therefrom so as to communicate with the syringe HS when the needle assembly NA is in place. The socket member SK may be provided with drive lugs LG for use in installing and/or removing the needle assembly NA on the hypodermic syringe HS. The needle tip NT is sharpened to facilitate use. The syringe HS has an appropriate plunger PL.

The needle cover assembly 10, as seen in FIGS. 1–8, includes generally arcuate clamp section 11 which is adapted to clip over the barrel BL of the syringe HS. It can be slidably moved along the length of the barrel as will become more apparent. The resiliency of the clamp section 11 is such that it grips the barrel BL sufficiently to hold it in the location desired. The clamp section 11 is connected to one end of an elongate resilient extension 12 which extends outwardly from the clamp section 11 generally parallel to the longitudinal axis $A_L$ of the opening through the clamp section 11. As will become more apparent, the extension 12 has a length $L_1$ which is greater than length of the needle assembly NA. That end of the extension 12 opposite the clamp section 11 is provided with a needle enclosure section 14. For sake of clarity, that end of the needle cover assembly 10 which projects in the same direction as the needle N will be called the forward end while the opposite end will be called the rear end.

The extension 12 includes a base section 16 at the rear end thereof which is generally parallel to the axis $A_L$ while the forward end of the base section 16 is provided with a connector section 18 which mounts the needle enclosure section 14 on the forward end thereof. The extension 12 tapers inwardly slightly from its rear end toward its forward end and curves to conform to the enclosure section 14 at its forward end.

The needle enclosure section 14 includes support section 20 connected to the connector section 18 and extending forwardly therefrom. The support section 20 mounts a solid body section 21 on the forward end thereof with the solid body section 21 having its central axis coincidin the axis $A_L$ when the needle cover assembly 10 is in its relaxed condition. The solid body section 21 has a generally circular cross-sectional shape and tapers inwardly slightly from its rear end toward its forward end. The solid body section 21 also defines a needle receiving passage 22 therein closed at its forward end and having a rearwardly facing opening 24 therein adapted to face the needle tip NT as will become more apparent. The needle receiving passage 22 includes an entry section 25 which tapers inwardly from diameter $d_1$ at opening 24 down to diameter $d_N$ at its forward end where it joins with the main section 26 of diameter $d_N$. The diameter $d_N$ is the diameter of the needle N. The main section 26 of the needle receiving passage 22 has a length $L_2$ which is greater than the cut portion of the needle tip NT so that a cylindrical portion of the needle N will fit into the passage 22 as will become more apparent. The difference betweed diameter $d_1$ and $d_N$ is selected to facilitate insertion of the needle tip NT into the passage 22 as will become more apparent.

The support section 20 is a tapered section that tapers down from its major diameter $d_2$ at its juncture with the extension 12 to the outside diameter $d_4$ of the solid body section 21 at its juncture therewith. The centerline of section 20 coincides with axis $A_L$ and that portion of the section 20 opposite extension 12 has been cut away along a chord to form a top surface 30 generally parallel to the axis $A_L$ located a distance $d_5$ from the axis $A_L$ of one-half the diameter $d_4$.

The section 20 also has a tapered guide passage 31 extending therethrough that tapers inwardly from diameter $d_6$ at its rear end to the diameter $d_1$ at its juncture with the entry section 26 of passage 22. The rear end of section 20 is cut away along a taper down to the connector section 18 on extension 12 to form a tapered end portion 32 on section 20 through which the passage 31 opens. The end portion 32 is cut along a vertical plane to form a slot 34 facing away from extension 12 that tapers inwardly from diameter $d_6$ to intermediate distance $d_8$ at the leading end of the end portion 32 corresponding to the diameter of passage 31 at that point.

The main portion 35 of section 20 is also formed with a radially extending slot 36 along the same plane as slot 34 so that the slots 34 and 36 have a common axis $A_{SL}$ as seen in FIG. 11. The plane of slots 34 and 36 is also perpendicular to the top surface 30. Slot 36 opens onto the surface 30 and has a width $W_{SL}$ corresponding to diameter $d_1$ at the entry section 25 of passage 22 in body section 21. The rear end of slot 36 opens into slot 34 while the forward end of slot 36 terminates at the rear end of solid body section 21. Slot 36 also opens into the guide passage 31 so that a needle can pass laterally through slot 36 into guide passage 31.

To assist in maintaining the needle N in alignment with the assembly 11 and the slots 34 and 36 while the needle N projects over the solid body section 21, a pair of spaced apart upstanding guide ears 40 are mounted on the rear end of section 21. The ears 40 are spaced apart at least the diameter of the needle N and are located equidistant on opposite sides of the axis $A_{SL}$. The height $h_1$ of the ears 40 is sufficient for a portion of the needle N to lie within the slots 34 and 36 before the ears 40 releases the needle.

To facilitate one-handed operation of the assembly 10, a gripping section 41 is provided on extension 12 adjacent the clamp section 11 and on that side of extension 12 facing away from axis $A_L$. Section 41 includes a pair of upstanding spaced apart end lugs 42 with intermediate gripping ridges 44 therebetween.

The assembly 10 is illustrated as being made in an one piece molded plastic construction. The natural resiliency of the plastic is sufficient to provide adequate operation thereof. It is to be understood that different constructions may be used without departing from the scope of the invention.

The needle cover assembly 110, seen in FIGS. 9, 10 and 13 is designed for use with a needle where the diameter of the part carrying the needle is larger than that for a hydrodermic syringe. An example of such an arrangement is a holder for vacuum containers for withdrawing blood and the like. The assembly 110 similarly to the assembly 10 includes a generally arcuate clamp section 111 which is adapted to clip over the holder mounting the needle to be covered so that it can be slidably moved along the length of the holder. An extension 112 extends outwardly from the clamp section 111 generally parallel to the longitudinal axis $A_L$ with a length greater than the length of the projecting portion of the needle assembly to be covered. The extension 112 mounts the needle enclosure section 114 thereon at that end opposite the clamp section 111.

The extension 112 includes base section 116 connected to the clamp section 111 with connector section 118 that extends from the foward end of the base section 116 inwardly toward the axis $A_L$ at a convenient angle so that the enclosure section 114 is centered on the axis $A_L$.

The needle enclosure section 114 as best seen in FIGS. 10 and 13 includes a solid body section 121 that is oriented coaxially with the axis $A_L$ when the cover assembly 110 is in its relaxed condition. The solid body section 121 is connected to the forward end of the connector section 118 and defines the needle receiving passage 122 therein closed at its forward end and having a rearwardly facing opening 124 at its rear end adpated to face the needle tip NT, as will become more apparent. The needle receiving passage 122 tapers inwardly from a major diameter $d_M$ at its rearend to a diameter $d_R$ at its forward end. The diameter $d_M$ is selected to allow the needle to freely enter the passage 122. The solid body section 121 also tapers inwardly from its rear end toward its forward end with a portion thereof cut away along a chord to form a top surface 130 generally parallel to axis $A_L$. The surface 130 is located on that side of the solid body section 121 opposite its connection with the extension 112. The solid body section 121 also defines a downwardly facing slot 136 opening onto the surface 130 centered in a plane perpendicular to the surface 130 and passing through axis $A_L$. The slot 136 opens onto the rear end of the solid body section 121 and terminates a distance $d_c$ from the leading end of the body section 121 where the distance $d_c$ is sufficient for that section of the passage 122 to cover the tip of the needle. The slot 136 has a width $W_L$ seen in FIG. 13 which is larger than the diameter of the needle with which the device is to be used to allow the needle to pass therethrough. It will further be noted from FIG. 13 that the slot 136 tapers inwardly from surface 130 to assist in guiding the needle therethrough.

To assist in maintaining the needle in alignment with the enclosure member 114, a pair of spaced apart upstanding guide ears 140 seen in FIGS. 10 and 13 are mounted on the body section 121 just forwardly of the forward end of the slot 136 with the ears 140 being located equidistance on opposite sides of the axis $A_L$. The height of the ears 140 is sufficient for a portion of the needle being used therewith to lie within the slot 136 before the ears 140 release the needle.

To facilitate one-handed operation of the assembly 110, a gripping section 141 is provided on the extension 112 adjacent the clamp section 11 and facing away from the axis $A_L$. Section 141 includes the upstanding, spaced apart end lugs 142 with intermediate gripping ridges 144 therebetween.

OPERATION

Figure 3:
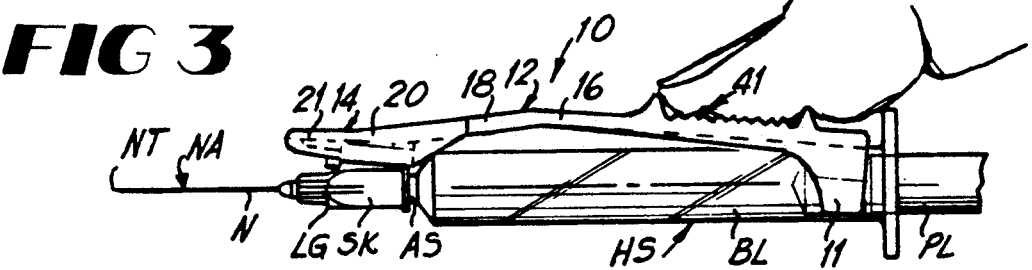
FIG. 3 is a side elevational view similar to FIG. 2 showing the invention retracted.
Figure 4:
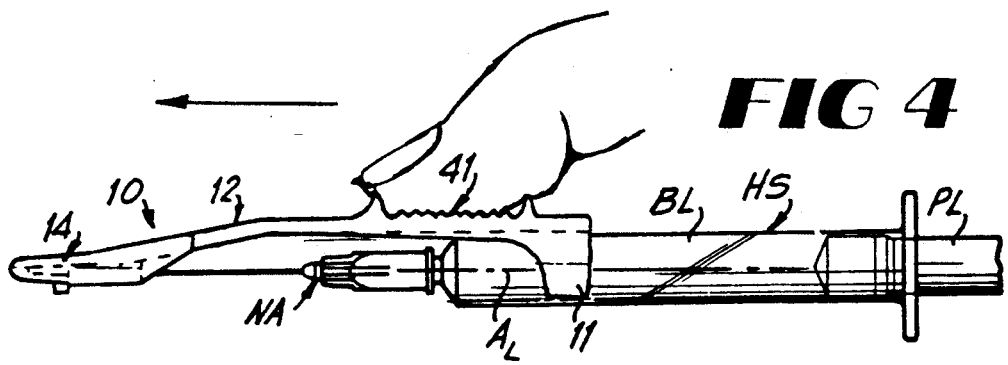
FIG. 4 is a view similar to FIG. 3 with the invention extended.
Figure 5:
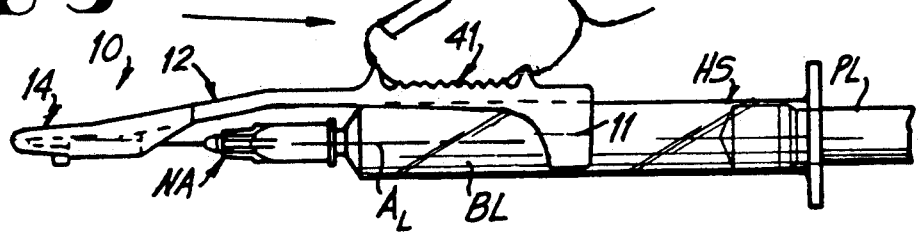
FIG. 5 is a view similar to FIG. 4 with the invention pulled over the needle.

As seen in FIGS. 2-5, the cover assembiy 10 is loaded onto the barrel of the hyprodermic syringe, usually prior to removal of the packaged needle cover NC supplied with the needle being used in the hyprodermic syringe. The assembly 10 is clamped onto the barrel of the syringe so that the needle enclosure section 14 lies adjacent the base of the needle assembly NA and does not interfer with the use of the needle N. After the clamp section 11 is clamped into place, the user will then remove the original needle cover NC and use the needle in the conventional manner. After the user uses the needle, the user grasps the hyprodermic syinge HS in a conventional manner, engages the gripping section 41 on the assembly and simply pushes forwardly on the assembly 10 as illustrated in FIG. 3. This causes the needle enclosure section 114 to slide along the length of the needle. The guide ears 40 serve to maintain alignment between the enclosure section 114 and the needle N as seen in FIG. 6. The user continues to push the needle cover assembly 10 along the barrel of the hypodermic syringe, as seen in FIG. 4, until the needle enclosure section 114 passes the tip NT of the needle and the needle N drops into the guide passage 31 through the slots 34 and 36 as seen in FIG. 7. The natural resiliency of the assembly 10 is such that the needle tip NT will now be generally in axial registration with the passage 22 in the solid body section 21. The user then pulls back on the gripping section 41 of the assembly 10 as seen in FIG. 5 with the guide passage 31 as well as the entry section 25 on the needle receiving passage 22 directing the tip NT of the needle into the main section 26 of the needle passage 22. The operator continues to pull back on the gripping section 41 until the needle N seats within the passage 22 as seen in FIG. 8. At that time, the operator simply releases the gripping section 41 and the needle cover assembly 10 remains in place. Because the needle N has a line-to-line fit with the passage 22, dripping of the material from the needle is prevented.

The needle cover assembly 110 is used similarly to the assembly 10. The clamp section 111 is placed over the barrel of the vacuum container housing (not shown) and manipulated similarly to assembly 10 to cover the needle on the vacuum container.

What is claimed as invention is:

1. A needle cover assembly for use with a needle assembly mounted in a support member comprising:
   clamping means for removably mounting said cover assembly on the support member;
   needle enclosure means defining a needle tip receiving passage therein adapted to receive the tip of the needle therein;
   extension means connecting said needle enclosure means with said clamping means so that said needle enclosure means can be moved relative to the needle tip whereby the needle tip can be inserted into said passage to cover same after use; and needle guide means on said needle enclosure means to maintain axial alignment between said needle enclosure means and the needle as said needle cover assembly is moved into operative position from a stowed position in which the needle is exposed for use.

2. The needle cover assembly of claim 1 wherein said needle tip receiving passage makes a line-to-line fit with the needle.

3. The needle cover assembly of claim 1 wherein said needle tip receiving passage is tapered to engage the needle tip.

4. The needle cover assembly of claim 1 wherein said needle enclosure means defines an elongate slot therein adapted to receive the needle tip laterally therethrough, said slot being in registry with said needle tip receiving passage to facilitate the insertion of the needle tip into said passage.

5. The needle cover assembly of claim 1 wherein said needle guide means include a pair of spaced apart guide ears located equidistance on opposite sides of the axis of said passage.

6. The needle cover assembly of claim 1 wherein said needle closure means further defines a tapered needle guide passage in registry with said needle tip receiving passage to facilitate the insertion of the needle tip into said needle tip receiving passage.

7. The needle cover assembly of claim 6 wherein said needle enclosure means defines an elongate slot therein adapted to receive the needle tip laterally therethrough, said slot extending into said guide passage to facilitate the insertion of the needle tip into said guide passage.

8. A needle cover assembly for use with a needle assembly cover assembly on the support comprising:

needle enclosure means defining a needle tip receiving passage therein adapted to receive the tip of the needle therein;

extension means connecting said needle enclosure means with said clamping means so that said needle enclosure means can be moved relative to the needle tip whereby the needle tip can be inserted into said passage to cover same after use; and, needle guide means on said needle enclosure means to maintain axial alignment between said needle enclosure means and the needle as said needle cover assembly is moved into operative position from a stowed position in which the needle is exposed for use; said needle guide means including a pair of spaced apart guide ears located equidistance on opposite sides of the axis of said slot.

9. The needle cover assembly of claim 8 wherein said needle tip receiving passage makes a line-to-line fit with the needle.

* * * * *